US006792309B1

(12) United States Patent
Noren

(10) Patent No.: US 6,792,309 B1
(45) Date of Patent: Sep. 14, 2004

(54) MULTI-SENSOR SYSTEM FOR CONTROLLING AN IMPLANTABLE HEART STIMULATOR

(75) Inventor: Kjell Noren, Solna (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/937,339

(22) PCT Filed: Mar. 7, 2000

(86) PCT No.: PCT/SE00/00450

§ 371 (c)(1),
(2), (4) Date: Sep. 21, 2001

(87) PCT Pub. No.: WO00/56397

PCT Pub. Date: Sep. 28, 2000

(30) Foreign Application Priority Data

Mar. 23, 1999 (SE) ................................ 9901056

(51) Int. Cl.[7] .......................... A61N 1/365; A61B 5/0215
(52) U.S. Cl. ......................................... 607/23; 600/486
(58) Field of Search ............................... 600/372–374, 600/377, 381, 485, 486, 488; 607/9, 17, 23

(56) References Cited

U.S. PATENT DOCUMENTS

| | | | |
|---|---|---|---|
| 4,600,017 A | 7/1986 | Schroeppel | |
| 4,860,751 A | 8/1989 | Callaghan | |
| 4,967,755 A | * 11/1990 | Pohndorf | ..................... 600/488 |
| 5,213,098 A | 5/1993 | Bennett et al. | |
| 5,271,408 A | 12/1993 | Breyer et al. | |
| 5,417,715 A | 5/1995 | Noren et al. | |
| 5,514,171 A | * 5/1996 | Hoegnelid et al. | ........... 607/122 |
| 5,628,777 A | 5/1997 | Moberg et al. | |
| 5,800,468 A | * 9/1998 | Holmstrom | ................... 607/17 |
| 5,843,135 A | * 12/1998 | Weijand et al. | ............... 607/17 |

OTHER PUBLICATIONS

"Two Years Follow–up on a $pO_2$–sensor Controlled Pacemaker: A Comparative Study in Healthy and AV–node Ablated Dogs," Holmström et al., Europace '97, 8th European Symposium on Cardiac Pacing, Athens Greece, Jun. 8–11, 1997, pp. 477–481.

"Long–term in vivo Experience of an Electrochemical Sensor Using the Potential Step Technique for Measurement of Mixed Venous Oxygen Pressure," Holmström et al., Biosensors and Bioelectronics, vol. 13, No. 12 (Dec. 1998), pp. 1287–1295.

* cited by examiner

Primary Examiner—Kennedy Schaetzle
Assistant Examiner—Kristen Droesch
(74) Attorney, Agent, or Firm—Schiff Hardin LLP

(57) ABSTRACT

A multi-sensor system for controlling an implantable heart stimulator, and an implantable heart stimulator containing such a multi-sensor system, have a piezoelectric pressure sensor adapted for placement in the blood stream of a subject, the piezoelectric pressure sensor having at least one electrode that is adapted for electrical contact with the blood stream, and an oxygen pressure sensor having a measurement electrode formed by the (at least one) electrode of the piezoelectric pressure sensor.

36 Claims, 3 Drawing Sheets

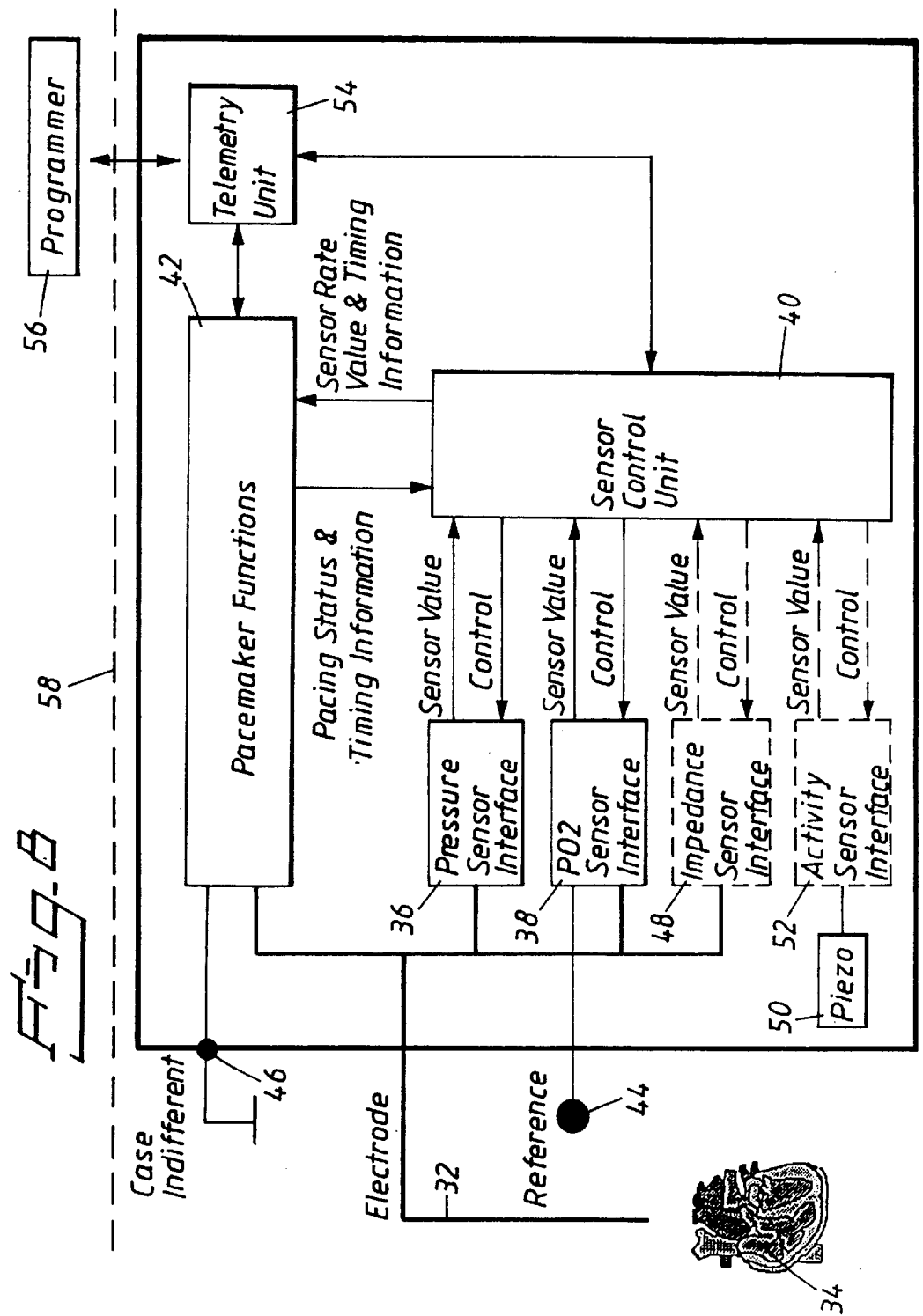

MULTI-SENSOR SYSTEM FOR CONTROLLING AN IMPLANTABLE HEART STIMULATOR

BACKGROUND OF THE INVENTION

1. Field of the Invention

The present invention relates to a multisensor system intended for controlling an implantable heart stimulator of the type having a piezoelectric pressure sensor adapted to be placed in the bloodstream of a living organism with at least one electrode adapted to be in electrical contact with said bloodstream.

2. Description of the Prior Art

In today's pacemaker systems different physiological sensors are often used for rate control and diagnostics.

An electrochemical blood oxygen pressure sensor is described in Holmström et al., "Two years follow up on a $pO_2$-sensor controlled pacemaker: A comparative study in healthy and AV-node ablated dogs", Europace '97, 8th European Symposium on Cardiac Pacing, Athens, Greece, 8–11 June, 1997, pp. 477–481, and Holmström et al., "Long term in vivo experience of an electrochemical sensor using potential step technique for measurement of mixed venous oxygen pressure", Biosensors and Bioelectronics, 13(12), December 1998, pp 1287–1295. This partial blood oxygen pressure sensor—$pO_2$—sensor—includes an electrode arrangement formed by a working electrode, a reference electrode and a counter electrode, this last mentioned electrode being formed by the heart stimulator housing.

A piezoelectric pressure sensor adapted to be placed in the bloodstream of a living organism is disclosed in e.g. U.S. Pat. No. 4,600,017, and in U.S. Pat. No. 5,271,408 a system for blood flow measurements within vascular vessel s or the heart is described. This system has two transducers, one of which has piezoelectric segments mounted on the exterior surface of a catheter with outer electrodes adapted to be in electrical contact with the bloodstream.

With the aid of multisensor systems it is possible to extract more information about the body's cardiac output need. A multisensor system for controlling a pacemaker is described in U.S. Pat. No. 5,213,098. The multisensor system according to this patent has two separated sensors, namely a ventricular or arterial blood pressure or flow sensor and a separate oxygen saturation sensor intended to be positioned in the coronary sinus. Such a multisensor system is, however, difficult to use and makes implantation complicated.

SUMMARY OF THE INVENTION

An object of the present invention is to provide a simple multisensor system including a piezoelectric pressure sensor and an oxygen pressure sensor, which avoids the drawbacks of the above-mentioned prior art multi-sensor system.

This object is achieved by a multisensor system intended for controlling an implantable heart stimulator which includes a piezoelectric pressure sensor adapted to be placed in the bloodstream of a living organism and at least one electrode adapted to be in electrical contact with the bloodstream, and wherein the electrode forms the measurement electrode of an oxygen pressure sensor.

In this manner existing electrode configurations of a heart stimulator are used for multisensor applications and a compact multisensor system of dual type is provided without changing the structure or mechanical properties of the stimulator electrode system.

In an embodiment of the sensor system according to the invention a signal processor is controlled to deliver as an output signal the pressure signal and the oxygen pressure signal from different selectable time windows of the cardiac cycle. Thus different time windows are selected for different kinds of measurements. The oxygen pressure measurement is a quick measurement and preferably is performed in a measurement window after the QRS-complex.

In the preferred embodiment the piezoelectric pressure sensor has a supporting structure provided with a layer of piezoelectric material. According to an embodiment of the sensor system of the invention the supporting structure of the pressure sensor includes one of the materials of titanium, titanium alloy, titanium nitride, platinum, platinum alloy, niobium, niobium alloy, tantalum, tantalum alloy or carbon, since all these materials are biocompatible.

These materials may for instance be used as a conducting layer between the piezoelectric layer and a non-conducting supporting structure, for improving the conductivity between the piezoelectric layer and the supporting layer and/or for improving the adhesion of the piezoelectric layer to the supporting structure. For improving the adhesion a thin layer (2–3 atom layers) of titanium or chrome-nickel is preferred.

In other embodiments of the sensor system of the invention, in which the piezoelectric element is provided with an outer electrically conducting layer which is covered by an electric insulation, a ring of the insulation is removed to form a ring-shaped measurement electrode of the oxygen pressure sensor or openings are made in said insulation to form the measurement electrode of the oxygen pressure sensor. This latter embodiment will increase the mechanical stability of the electrode.

In other embodiments of the sensor system provided for sensing the impedance between the measurement electrode and the reference electrode and supplying a corresponding impedance signal to the signal processor for selectable separation of the pressure, oxygen pressure and impedance signals, a depolarization sensor can be provided for sensing depolarization signals picked up by the measurement electrode. This depolarization sensor supplies a corresponding depolarization signal to the signal processor for selectable separation of the pressure, oxygen pressure, impedance and depolarization signals. Thus, in this way the multisensor system according to the invention is extended to include measurement of the parameters electrical impedance and depolarization without complicating or otherwise modifying the existing stimulator electrode configuration.

DESCRIPTION OF THE DRAWINGS

FIG. 8 is a block diagram of an example of an implantable heart stimulator provided with a multisensor system according to the invention.

DESCRIPTION OF THE PREFERRED EMBODIMENTS

Figure 1:
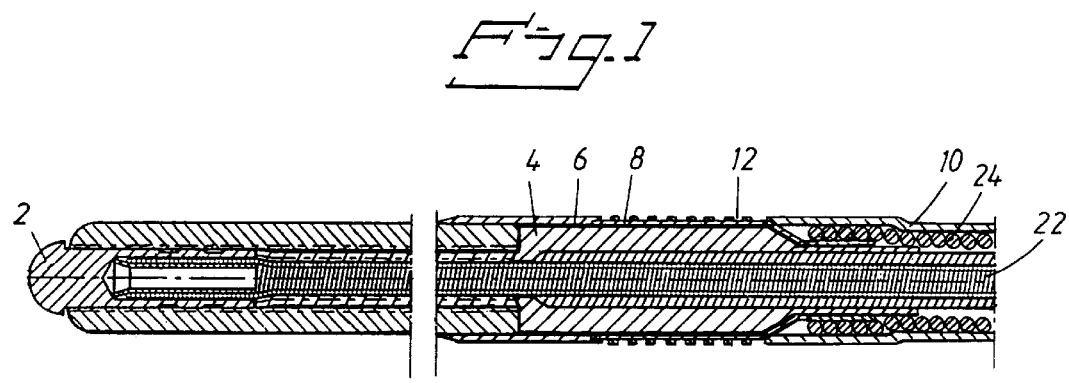
FIG. 1 shows a longitudinal section through a part of a pacemaker lead provided with an embodiment of the multisensor system according to the invention.

FIG. 1 shows a longitudinal section of a part of a lead for an implantable heart stimulator with a tip electrode 2 at the distal lead end. The lead is provided with a dual pressure and pO$_2$-sensor according to a first embodiment of the multi-sensor system according to the invention. The dual sensor has a supporting structure in the form of a conductive tube 4 covered with a layer of e.g., titanium alloy, titanium nitride, platinum, platinum alloy, niobium, niobium alloy, tantalum, tantalum alloy or carbon, which on its outer surface is covered with a layer or film 6 of a piezoelectric material, preferably a ceramic piezoelectric material. On the outer surface of the piezoelectric film 6 a layer 8 of a conductive material is applied. In this way the tube 4 and the layer 8 are forming electrodes for picking up the charge produced in the piezoelectric film 6, when it is subject to pressure variations, for producing a corresponding pressure signal. The lead further has an outer silicone rubber insulation 10.

In the embodiment shown in FIG. 1 circular openings 12 are formed in the insulating silicone rubber 10 to enable an electrochemical contact of the conductive layer 8 with blood. In this way the conductive layer 8 forms the measurement electrode for the pO$_2$-measurements.

The conductive supporting structure 4 forms the inner electrode of the pressure sensor and is electrically connected to the inner conductor coil 22 of the lead in the contact area to the left of FIG. 1.

Figure 2:
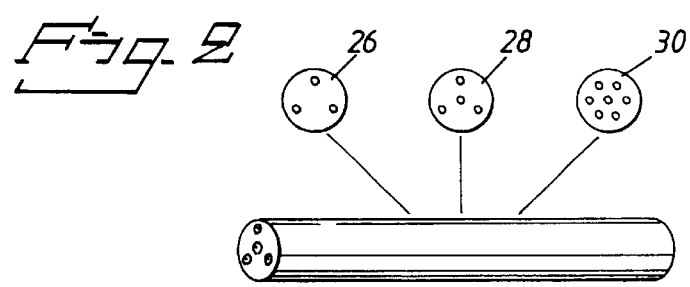
FIG. 2 shows in cross-section and longitudinal view a part of a lead designed to contain several parallel conductors.

The outer conductive layer 8 which forms the outer electrode of the pressure sensor and the measurement electrode of the pO$_2$-sensor is in electrical contact with the outer conducting coil 24 of a lead in the contact area to the right in FIG. 2. Between these contact areas there is a sensing area where the rubber insulation 10 is partly removed to enable electro-chemical contact between the conductive layer 8 and blood for the pO$_2$-measurement, as described above. The extension of each of the contact areas and the sensing area in the longitudinal direction of the lead can typically be about 3 mm.

The thickness of the conducting layer 8 is typically 5–10 mm and this layer is made of e.g. gold or carbon.

The outer conducting layer 8 in the above described embodiment of the multisensor system according to the invention thus also forms the measurement or working electrode of a pO$_2$ sensor of the kind described in the above mentioned two articles by Holmström et al, "Two years follow up on a pO$_2$ sensor controlled pacemaker: A comparative study in healthy and AV-node ablated dogs, Europace '97, 8th European Symposium on Cardiac Pacing, Athens, Greece, 8–11 June, 1997, pp. 477–481, and "Long term in vivo experience on an electrochemical sensor using the potential step technique for measurement of mixed venous oxygen pressure", Biosensors and Bioelectronics, I3(12) December, 1998, pp. 1287–1295, with a reference electrode of carbon placed e.g. in the header of the pulse generator of a heart stimulator and the stimulator case being used as counter-electrode.

Figure 3:
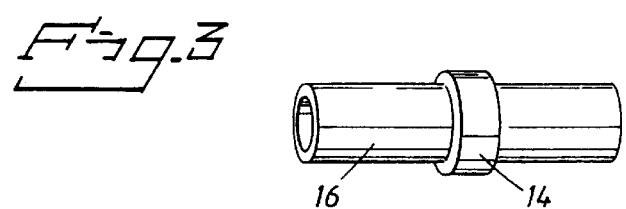
FIG. 3 shows in perspective view an embodiment of a dual sensor sensing element with a gold ring electrode as measurement electrode of a $pO_2$-sensor.
Figure 4:
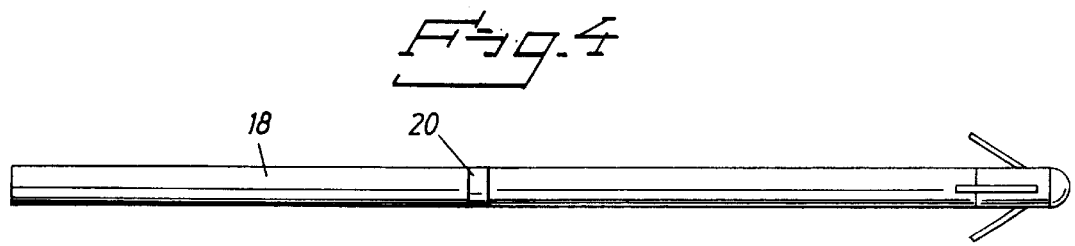
FIG. 4 illustrates a lead provided with the sensor element of FIG. 3.

By breaking the electrode rubber insulation 10 in the form of circular openings 12 the mechanical stability of the conducting layer 8, serving as electrode, is increased. However, this design also introduces damping of the pressure signal. To avoid this inconvenience a ring-shaped portion of the rubber insulation can be removed to expose a ring-shaped electrode 14, which is in contact with a annular pressure sensing element 16, see FIG. 3. This pressure sensing element 16 is mounted in a lead 18 with the ring electrode 14 exposed for contacting the blood to form the measurement electrode of the pO$_2$-sensor, as illustrated as 20 in FIG. 4.

FIG. 2 shows in perspective view and in cross-sections a part of alternative embodiments of the lead designed to contain several parallel conductors instead of multiple coaxially arranged spirals. This is a convenient way of making an increase of the number of conductors in the lead possible. In FIG. 2 tri-lumen 26, quadro-lumen 28 and heptal-lumen 30 embodiments are shown as examples. As the number of conductors can be easily increased in this embodiment two separate conductors can preferably be provided for the dual sensor according to the present invention described in connection with FIG. 1.

Figure 5:
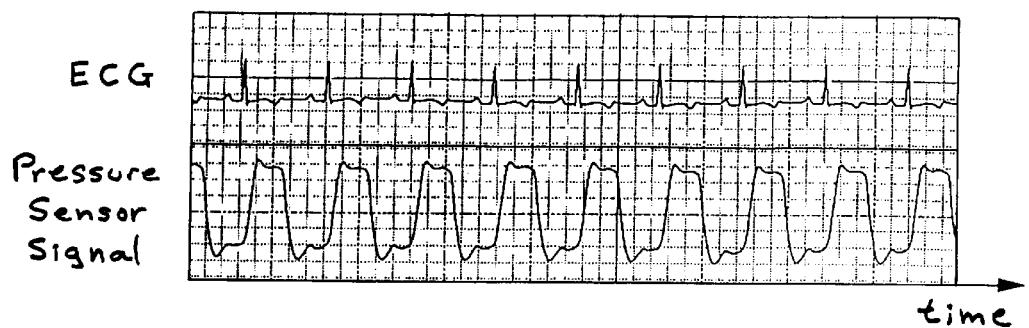
FIGS. 5–7 show different examples of pressure measurements performed on a dog with a dual sensor system as shown in FIG. 1.
Figure 6:
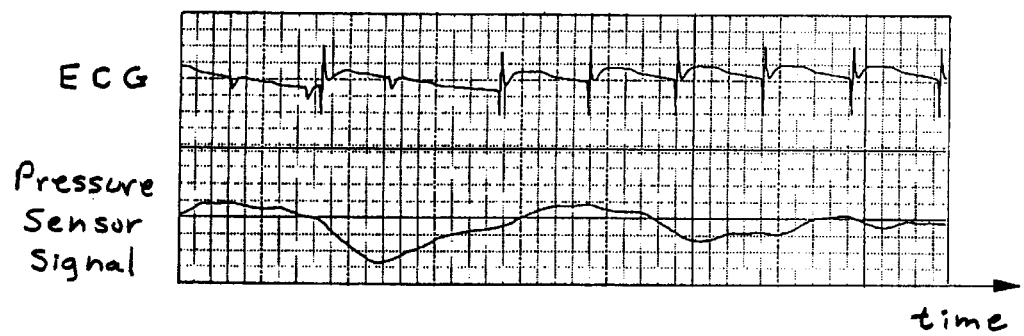
Figure 7:
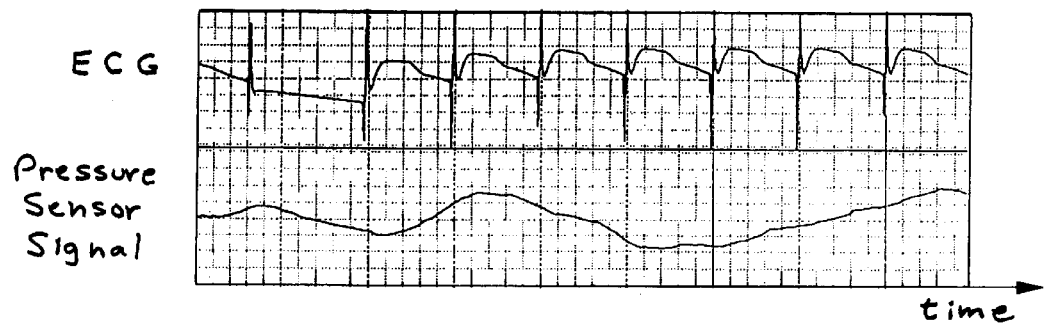

FIGS. 5–7 show examples of surface ECG's and invasive pressure signals recorded from the pressure sensor of a dual sensor as described above.

FIG. 5 shows the surface ECG for a spontaneous heart rate of 125 beats per minute and the pressure signal from the sensor positioned in the center of the right ventricle. The time scale is 100 ms per division. As can be seen, FIG. 5 illustrates a very stable situation.

FIG. 6 shows the corresponding signals recorded for a situation with DDD pacing with a rate of 120 beats per minute and the sensor positioned in the right atrium. In this case the dominating part of the pressure variation is the respiratory modulation.

FIG. 7 illustrates a situation with DDD pacing with a rate of 115 beats per minute and the sensor being positioned in vena cava.

As can be seen from FIGS. 5–7 the pressure signal is a comparatively slowly varying signal, whereas the pO$_2$-measurement is a quick measurement, a measurement pulse of the order of 10 ms being used. Different time windows can therefore easily be selected for recording the pressure and the pO$_2$-signals respectively. The time window for the pO$_2$-measurement can suitably be synchronized to the detection of the QRS-complex while the pressure signal is recorded during the remaining part of the cardiac cycle. Of course, only pO$_2$-measurements or only pressure measurements can be performed for several consecutive cardiac cycles.

FIG. 8 is a block diagram of a heart stimulator having pacemaker function and a multisensor system according to the present invention.

By an electrode, schematically shown at 32, implanted into the heart 34 of a patient, pressure signals and pO$_2$-signals are picked up as described above. These signals are supplied to a pressure sensor interface 36 and a pO$_2$-sensor interface 38. Corresponding sensed pressure and pO$_2$-values are fed to a sensor control unit 40 which is controlling the pacemaker functions by delivering corresponding sensor rate value and timing information to the pacemaker unit 42.

The sensor control unit 40 thus provides the interface to the different sensors and controls the measurement timing and weighting of the obtained sensor values. The pacemaker unit 42 provides in its turn the sensor control unit 40 with pacing status and timing information, such as e.g. the detection of a spontaneous QRS-complex or if a stimulation pulse is delivered to the heart 34, by the lead 32. The time for the pO$_2$-measurement can thus be controlled from the sensor control unit 40 to be synchronized to a time window connected to such an event, like the detection of a QRS, as explained above, while the pressure sensor can be active during the remaining part of the cardiac cycle. Of course, the multisensor system can be controlled to only measure the pressure signal or the pO$_2$-signal for a selected number of consecutive cardiac cycles.

The sensor control unit 40 can provide the pacemaker unit 42 with a sensor rate value for the control of the stimulation rate of the pacemaker. Thus the pO$_2$-signal can be used for the controlling of the rate responsive rate while the pressure can be used for capture verification for delivery of corresponding timing information to the pacemaker unit 42.

The reference electrode, preferably positioned in the header of the pacemaker, as mentioned above, and the counter electrode, preferably formed by the stimulator case for being locked to the stimulator battery ground, are schematically shown at 44 and 46 respectively.

By positioning the dual sensor described above in the right atrium of the heart 34 oxygen in mixed venous blood is measured by the pO$_2$-measurement. The pressure measurement in the right atrium can be used to provide information about non-optimal pacing indicated by abnormally high pressure peaks, for instance at a pacemaker syndrome situation in a VVI system. The pressure measurements also can be used for detecting spontaneous atrial activity and atrial fibrillation due to non-synchronous stimulation in the right ventricle.

By positioning the dual sensor in the right ventricle pressure timing information can be used to determine the correct time for delivering the next stimulation pulse, see e.g. U.S. Pat. No. 5,417,715. A calculation of the pressure gradient dP/dt will then also give information about cardiac contractility.

By locating the described dual sensor in vena cava, pressure peaks in the vena cava, so called cannon waves, due to non-synchronous stimulation in the right ventricle, can be detected. The dual sensor can also be positioned in coronary sinus to measure coronary sinus pressure and oxygen content, which will be of value for the detection of e.g. ischemia. In general the multisensor system according to the invention will be of importance for detecting cardiac heart failures of patients having heart muscle ischemia and decreased pumping effect.

The multisensor system according to the invention also can include impedance and activity sensors. For the impedance measurement the same electrodes can be used as for the above described dual sensor. Thus the impedance also can be measured between e.g. the measurement electrode 8 of FIG. 1 and the reference electrode 44 used for the pO$_2$-measurements. The impedance can also be measured between e.g. the electrode tip 2, see FIG. 1, and the stimulator case, see 46 in FIG. 8.

The impedance signals are supplied to an impedance sensor interface 48 for delivery of corresponding sensor values to the sensor control unit 40 for use in the control of the pacemaker functions. Control signals are transferred in the opposite direction from the sensor control unit 40 to the impedance sensor interface 48 for controlling the impedance measurements.

In FIG. 8 an activity sensor in the form of a piezoelectric element 50 is also shown. The activity sensor 50 is also connected to the sensor control unit 40 via an activity sensor interface 52 for delivery of activity sensor values for use in the control of the pacemaker functions. Control signals are transmitted from the sensor control unit 40 to the activity sensor interface 52 for controlling the activity measurements.

The activity sensor has normally a fast response to the start of a physical exercise and can thus provide a fast rate response. The impedance sensor is used for instance to extract the respiration minute volume and frequency.

The sensor control unit can include circuits of different complexity ranging from simple timing and multiplexing functions all the way to sensor value weighting using fuzzy logic or neural networks.

As shown in FIG. 8 the implanted heart stimulator has a telemetry unit 54 for communication with an external programmer 56, the skin of the patient being indicated by the dashed line 58. In this way the programmer 56 communicates via the telemetry unit 54 with the pacemaker unit 42 and the sensor control unit 40 for receiving and transmitting information and data related to the operation of the heart stimulator.

One example of a measurement scenario obtained with the multisensor system according to the invention could be that a low or intermediate activity is measured by the activity sensor, a high respiration frequency with small amplitude is obtained from impedance measurements, low pO$_2$-values forming an indication for rate increase are measured with the pO2-sensor, and low contractility compared to rest values is detected from dP/dt obtained from blood pressure measurements. Such a scenario may be an indication of coronary insufficiency with an ongoing angina attack depending on heart muscle ischemia. In such a situation pacing should not be increased since there is a risk to then end up in a more severe situation such as infarction or fibrillation.

It should be noted that, although the invention has been described in connection with a pressure sensor comprising a supporting structure covered with a piezoelectric layer it could also be used in connection with any piezoelectric sensor adapted to be in contact with the bloodstream and comprising at least one electrode adapted to be in electrical contact with said bloodstream.

Although modifications and changes may be suggested by those skilled in the art, it is the intention of the inventor to embody within the patent warranted hereon all changes and modifications as reasonably and properly come within the scope of his contribution to the art.

What is claimed is:

1. A multi-sensor system for controlling an implantable heart stimulator, said multi-sensor system comprising:
   a piezoelectric pressure sensor adapted for placement in the blood stream of a living subject, said pressure sensor having at least one electrode adapted for electrical contact with said blood stream; and
   an oxygen pressure sensor having a plurality of electrodes including a measurement electrode, said measurement electrode being formed by said at least one electrode of said pressure sensor.

2. A multi-sensor system as claimed in claim 1 wherein said at least one electrode emits an electrical pressure signal received from said pressure sensor and an electrical oxygen pressure signal received from said oxygen pressure sensor, and wherein said multi-sensor system further comprises a signal processor connected to said pressure sensor and to said oxygen pressure sensor for separating said pressure signal from said oxygen pressure signal.

3. A multi-sensor system as claimed in claim 2 wherein said signal processor emits an output signal comprised of said pressure signal and said oxygen pressure signal from respectively different selectable time windows of a cardiac cycle of said subject.

4. A multi-sensor system as claimed in claim 3 wherein said oxygen pressure sensor further has a reference electrode, and wherein said multi-sensor system further comprises an impedance sensor for sensing electrical impedance between said measurement electrode and said reference electrode, said impedance sensor being connected to said signal processor and supplying an impedance signal thereto, and said signal processor selectively separating said pressure signal, said oxygen pressure signal and said impedance signal.

5. A multi-sensor system as claimed in claim 3 further comprising an activity sensor which senses activity of said subject and which supplies an activity signal to said signal processor, said signal processor selectively separating said pressure signal, said oxygen pressure signal and said activity signal.

6. A multi-sensor system as claimed in claim 3 further comprising a depolarization sensor for sensing depolarization activity picked up by said measurement electrode, said depolarization sensor supplying a depolarization signal corresponding to said depolarization activity to said signal processor, and said signal processor selectively separating said pressure signal, said oxygen pressure signal and said depolarization signal.

7. A multi-sensor system as claimed in claim 3 wherein said oxygen pressure sensor comprises a reference electrode, and wherein said multi-sensor system further comprises an impedance sensor for sensing electrical impedance between said measurement electrode and said reference electrode, said impedance sensor supplying an impedance signal corresponding to said electrical impedance to said signal processor, an activity sensor which senses activity of said subject and which supplies an activity signal corresponding to said activity to said signal processor, a depolarization sensor which senses depolarization activity picked up by said measurement electrode, said depolarization sensor supplying a depolarization signal corresponding to said depolarization activity to said signal processor, and said signal processor selectively separating said pressure signal, said oxygen pressure signal, said impedance signal, said activity signal and said depolarization signal.

8. A multi-sensor system as claimed in claim 1 wherein said measurement electrode comprises a layer formed of material selected from the group consisting of gold and carbon.

9. A multi-sensor system as claimed in claim 1 wherein said piezoelectric pressure sensor comprises an annular supporting structure having an outer surface, and a piezoelectric element disposed on at least a portion of said outer surface.

10. A multi-sensor system as claimed in claim 9 wherein said piezoelectric element comprises a layer of piezoelectric material on said outer surface of said supporting structure.

11. A multi-sensor system as claimed in claim 10 wherein said piezoelectric element comprises a tube of said piezoelectric material surrounding said support structure.

12. A multi-sensor system as claimed in claim 10 wherein said piezoelectric element comprises a ring of said piezoelectric material surrounding said supporting structure.

13. A multi-sensor system as claimed in claim 9 wherein said supporting structure is formed of material selected from the group consisting of titanium, a titanium alloy, titanium nitride, platinum, a platinum alloy, niobium, a niobium alloy, tantalum, a tantalum alloy, and carbon.

14. A multi-sensor system as claimed in claim 9 wherein said piezoelectric element is formed by an annular layer of piezoelectric material surrounding said outer surface of said supporting structure, and wherein said piezoelectric element has an outer surface, and wherein said measuring electrode comprises a ring surrounding said outer surface of said piezoelectric element.

15. A multi-sensor system as claimed in claim 14 wherein said piezoelectric element has an electrically conducting layer covered by an electrical insulation, with a ring of said electrical insulation being removed to form said measurement electrode.

16. A multi-sensor system as claimed in claim 9 wherein said piezoelectric pressure sensor comprises an annular layer of piezoelectric material surrounding said supporting structure, and wherein said piezoelectric element has circumferential sensitivity.

17. A multi-sensor system as claimed in claim 9 wherein said piezoelectric element has an electrically conducting layer covered by an electrical insulation, and wherein said electrical insulation has a plurality of openings therein forming said measurement electrode of said oxygen pressure sensor.

18. An implantable heart stimulator comprising:
a pulse generator which emits stimulation pulses;
a control unit connected to said pulse generator for controlling emission of said stimulation pulses from said pulse generator;
an electrode lead connected to said pulse generator adapted for implantation in the blood stream of a living subject;
a piezoelectric pressure sensor disposed in said lead and comprising at least one electrode adapted for electrical contact with said blood stream;
an oxygen pressure sensor disposed in said lead having a measurement electrode formed by said at least one electrode of said piezoelectric pressure sensor;
said piezoelectric pressure sensor emitting a pressure signal and said oxygen pressure sensor emitting an oxygen pressure signal; and
a signal processor connecting to said piezoelectric pressure sensor and to said oxygen pressure sensor for receiving said pressure signal and said oxygen pressure signal respectively therefrom, said signal processor selectively separating said pressure signal and said oxygen pressure signal and generating a processor output signal dependent on said pressure signal and said oxygen pressure signal, said signal processor being connected to said control unit and supplying said processor output signal thereto, said control unit controlling said pulse generator dependent on said processor output signal.

19. An implantable heart stimulator as claimed in claim 18 further comprising a stimulator housing containing said pulse generator, said control unit and said signal processor, and wherein said oxygen pressure sensor comprises a reference electrode on an exterior of said stimulator housing.

20. An implantable heart stimulator as claimed in claim 18 further comprising a stimulator housing containing said pulse generator, said control unit and said signal processor, and wherein said oxygen pressure sensor has a counter-electrode formed by said stimulator housing.

21. An implantable heart stimulator as claimed in claim 18 wherein said electrode lead is a bipolar lead having an inner insulating layer and an outer insulating layer coaxially disposed relative to each other, and wherein said piezoelectric pressure sensor is disposed between said inner insulating layer and said outer insulating layer.

22. An implantable heart stimulator as claimed in claim 18 wherein said signal processor emits an output signal comprised of said pressure signal and said oxygen pressure signal from respectively different selectable time windows of a cardiac cycle of said subject.

23. An implantable heart stimulator as claimed in claim 22 wherein said oxygen pressure sensor further has a reference electrode, and wherein said implantable heart stimulator multi-sensor system further comprises an impedance sensor for sensing electrical impedance between said measurement electrode and said reference electrode, said impedance sensor being connected to said signal processor and supplying an impedance signal thereto, and said signal processor selectively separating said pressure signal, said oxygen pressure signal and said impedance signal.

24. An implantable heart stimulator as claimed in claim 22 further comprising an activity sensor which senses activity of said subject and which supplies an activity signal to said signal processor, said signal processor selectively separating said pressure signal, said oxygen pressure signal and said activity signal.

25. An implantable heart stimulator as claimed in claim 22 further comprising a depolarization sensor for sensing depolarization activity picked up by said measurement electrode, said depolarization sensor supplying a depolarization signal corresponding to said depolarization activity to said signal processor, and said signal processor selectively separating said pressure signal, said oxygen pressure signal and said depolarization signal.

26. An implantable heart stimulator as claimed in claim 22 wherein said oxygen pressure sensor comprises a reference electrode, and wherein said implantable heart stimulator multi-sensor system further comprises an impedance sensor for sensing electrical impedance between said measurement electrode and said reference electrode, said impedance sensor supplying an impedance signal corresponding to said electrical impedance to said signal processor, an activity sensor which senses activity of said subject and which supplies an activity signal corresponding to said activity to said signal processor, a depolarization sensor which senses depolarization activity picked up by said measurement electrode, said depolarization sensor supplying a depolarization signal corresponding to said depolarization activity to said signal processor, and said signal processor selectively separating said pressure signal, said oxygen pressure signal, said impedance signal, said activity signal and said depolarization signal.

27. An implantable heart stimulator as claimed in claim 18 wherein said measurement electrode comprises a layer formed of material selected from the group consisting of gold and carbon.

28. An implantable heart stimulator as claimed in claim 18 wherein said piezoelectric pressure sensor comprises an annular supporting structure having an outer surface, and a piezoelectric element disposed on at least a portion of said outer surface.

29. An implantable heart stimulator as claimed in claim 28 wherein said piezoelectric element comprises a layer of piezoelectric material on said outer surface of said supporting structure.

30. An implantable heart stimulator as claimed in claim 29 wherein said piezoelectric element comprises a tube of said piezoelectric material surrounding said support structure.

31. An implantable heart stimulator as claimed in claim 29 wherein said piezoelectric element comprises a ring of said piezoelectric material surrounding said supporting structure.

32. An implantable heart stimulator as claimed in claim 28 wherein said supporting structure is formed of material selected from the group consisting of titanium, a titanium alloy, titanium nitride, platinum, a platinum alloy, niobium, a niobium alloy, tantalum, a tantalum alloy, and carbon.

33. An implantable heart stimulator as claimed in claim 28 wherein said piezoelectric element is formed by an annular layer of piezoelectric material surrounding said outer surface of said supporting structure, and wherein said piezoelectric element has an outer surface, and wherein said measuring electrode comprises a ring surrounding said outer surface of said piezoelectric element.

34. An implantable heart stimulator as claimed in claim 33 wherein said piezoelectric element has an electrically conducting layer covered by an electrical insulation, with a ring of said electrical insulation being removed to form said measurement electrode.

35. An implantable heart stimulator as claimed in claim 28 wherein said piezoelectric pressure sensor comprises an annular layer of piezoelectric material surrounding said supporting structure, and wherein said piezoelectric element has circumferential sensitivity.

36. An implantable heart stimulator as claimed in claim 28 wherein said piezoelectric element has an electrically conducting layer covered by an electrical insulation, and wherein said electrical insulation has a plurality of openings therein forming said measurement electrode of said oxygen pressure sensor.

* * * * *